(12) United States Patent
Grafenberg

(10) Patent No.: US 10,448,003 B2
(45) Date of Patent: Oct. 15, 2019

(54) SYSTEM AND METHOD FOR TRIANGULATION-BASED DEPTH AND SURFACE VISUALIZATION

(71) Applicant: SIEMENS AKTIENGESELLSCHAFT, Munich (DE)

(72) Inventor: Alexander Grafenberg, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 392 days.

(21) Appl. No.: 14/674,139

(22) Filed: Mar. 31, 2015

(65) Prior Publication Data

US 2015/0281680 A1 Oct. 1, 2015

(30) Foreign Application Priority Data

Mar. 31, 2014 (DE) .................. 10 2014 206 004

(51) Int. Cl.
*H04N 13/344* (2018.01)
*H04N 13/156* (2018.01)
(Continued)

(52) U.S. Cl.
CPC ......... *H04N 13/344* (2018.05); *A61B 6/4441* (2013.01); *A61B 6/462* (2013.01); *A61B 6/5247* (2013.01); *G06T 19/006* (2013.01); *H04N 13/156* (2018.05); *H04N 13/167* (2018.05); *H04N 13/221* (2018.05);
(Continued)

(58) Field of Classification Search
USPC ........................................... 348/42
See application file for complete search history.

(56) References Cited

U.S. PATENT DOCUMENTS 5,091,926 A 2/1992 Horton et al.
6,608,884 B1 8/2003 Mazess et al.
(Continued)

FOREIGN PATENT DOCUMENTS

WO 2011063266 A2 5/2011
WO 2011134083 A1 11/2011
(Continued)

OTHER PUBLICATIONS

Sielhorst, Tobias, et al.: "Advanced Medical Displays: A Literature Review of Augmented Reality;" Journal of Display Technology; IEEE, New York, US; Bd. 4; Nr.4; pp. 451-467; XP011237912; ISSN: 1551-319X; DOI: 10.1109/JDT.2008.2001575; 2008.
(Continued)

*Primary Examiner* — Mikhail Itskovich
(74) *Attorney, Agent, or Firm* — Laurence Greenberg; Werner Stemer; Ralph Locher

(57) ABSTRACT

An intraoperative, marker-less visualization system and method for visualizing three-dimensional surface structures and depth structures of a patient during an intervention. A C-arm carries a C-arm projection module and a camera, and visualization spectacles include an HMD (head-mounted device) projection module and a camera. The projection modules serve for projecting structured light. A processor computes a combined image data set in order to project the latter onto spectacle lenses of the visualization spectacles.

12 Claims, 2 Drawing Sheets

(51) Int. Cl.
    *H04N 13/167*     (2018.01)
    *H04N 13/282*     (2018.01)
    *H04N 13/296*     (2018.01)
    *A61B 6/00*     (2006.01)
    *G06T 19/00*     (2011.01)
    *H04N 13/221*     (2018.01)
    *G02B 27/01*     (2006.01)

(52) U.S. Cl.
    CPC ......... *H04N 13/282* (2018.05); *H04N 13/296* (2018.05); *A61B 6/466* (2013.01); *G02B 27/017* (2013.01)

(56) References Cited

U.S. PATENT DOCUMENTS

| | | | |
|---|---|---|---|
| 9,513,113 B2* | 12/2016 | Yang | G01B 11/2513 |
| 2002/0082498 A1* | 6/2002 | Wendt | G06F 19/3406 600/411 |
| 2009/0034820 A1 | 2/2009 | Sugiyama | |
| 2013/0016185 A1* | 1/2013 | Stolka | A61B 1/041 348/46 |
| 2013/0021373 A1 | 1/2013 | Vaught et al. | |
| 2013/0060146 A1 | 3/2013 | Yang et al. | |

FOREIGN PATENT DOCUMENTS

| | | |
|---|---|---|
| WO | 2014005225 A1 | 1/2014 |
| WO | 2014037953 A2 | 3/2014 |

OTHER PUBLICATIONS

Peters, Terry M.: "Topical Review; Image-guidance for surgical procedure;" Physics in Medicine and Biology Institute of Physics Publishing; Bristol, GB; Bd. 51; Nr. 14; pp. R505-R540; XP020095863; ISSN: 0031-9155; DOI: 10.1088/0031-9155/51/14/R01; 2006.
Prathap Nair et al., "Matching 3D Faces with Partial Data" BMVC 2008 doi:10.5244/C.22.102.
D. Akca, "A New Algorithm for 3D Surface Matching", Institute of Geodesy and Photogrammetry, Swiss Federal Institute of Technology (ETH) Zurich.
T. Funkhouser et al. "Partial Matching of 3D Shapes with Priority-Driven Search", Eurographics Symposium on Geometry Processing (2006).
OMC—Optical Metrology Centre, "OMC Technical Brief—Single point optical triangulation", 2001.

\* cited by examiner

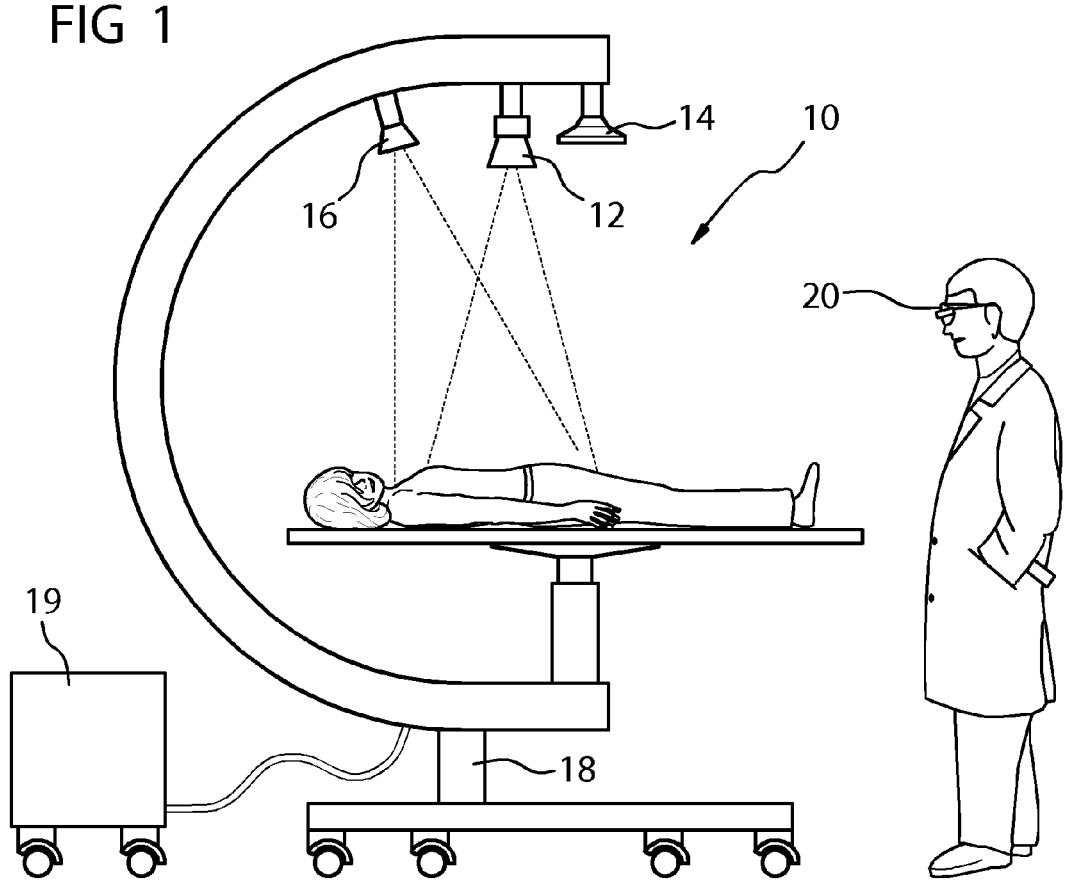
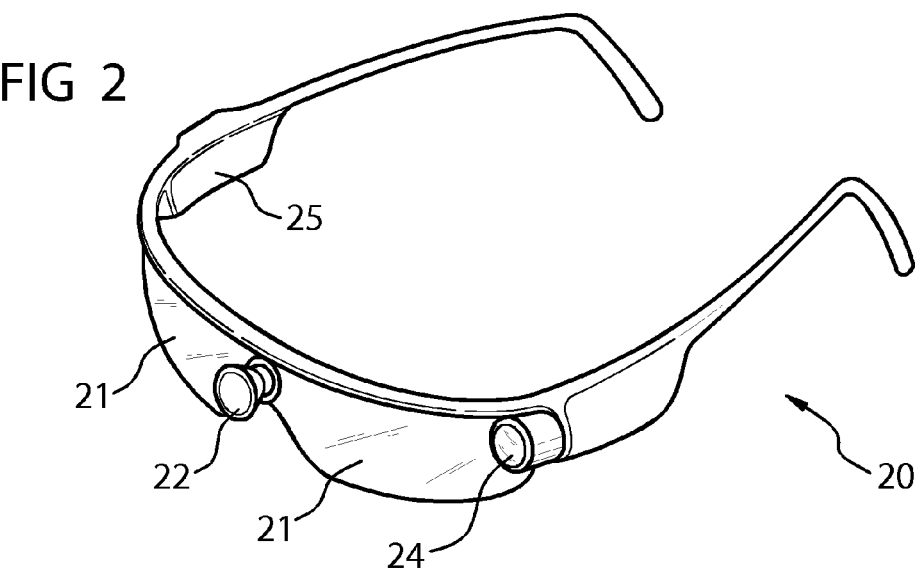

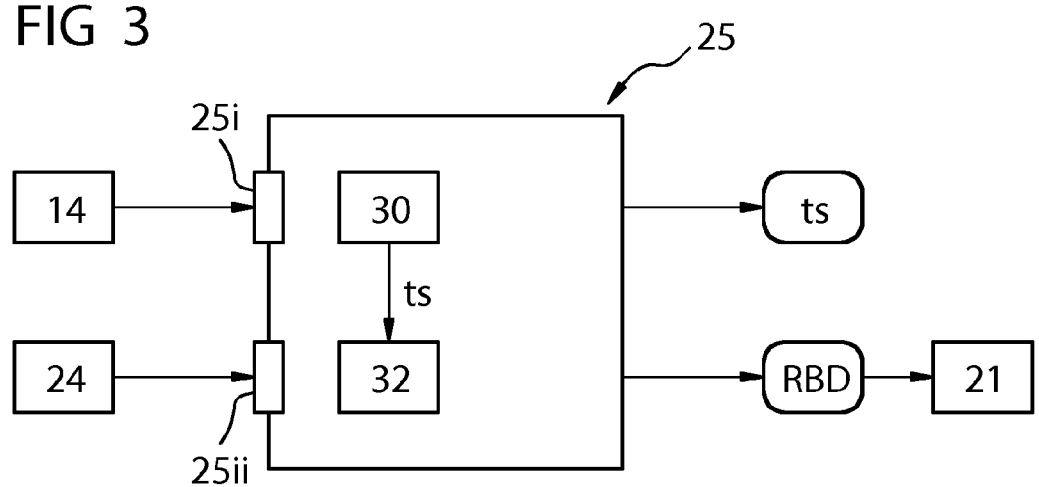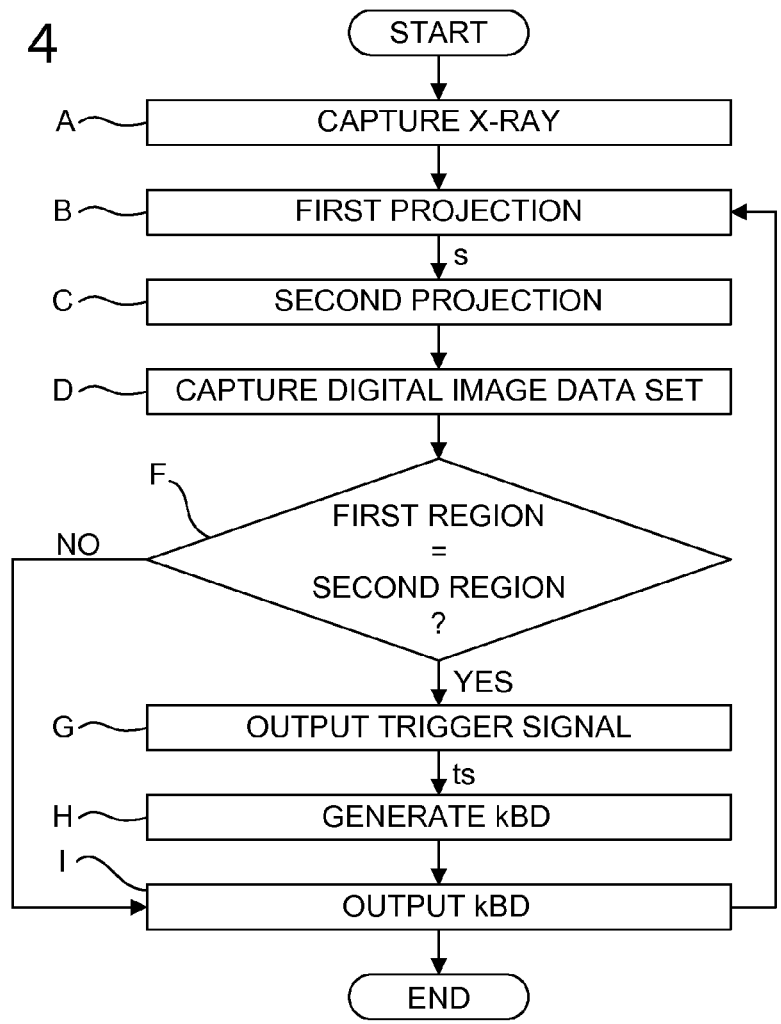

SYSTEM AND METHOD FOR TRIANGULATION-BASED DEPTH AND SURFACE VISUALIZATION

CROSS-REFERENCE TO RELATED APPLICATION

This application claims the priority, under 35 U.S.C. § 119, of German patent application DE 10 2014 206 004.4, filed Mar. 31, 2014; the prior application is herewith incorporated by reference in its entirety.

BACKGROUND OF THE INVENTION

Field of the Invention

The present invention lies in the field of intraoperative visualization techniques for visualizing medical structures (e.g., bones, organs or implants) inside the body of the patient and thus "in the depth," in particular using X-ray-based methods and for visualizing surface structures of the body surface. The invention can preferably be used in intraoperative interventions.

Navigation systems are known in the prior art that allow three-dimensional guidance of the physician in a targeted fashion when carrying out a medical intervention. However, it is necessary here to provide, in addition to the imaging device, further modules which are required within the context of the navigation system. This relates in particular to the provision of separate cameras with corresponding supply lines and network connections. However, these can negatively limit the moveability of the physician during the intervention, and not rarely result in significant time loss. The use of markers (e.g. infrared or passive markers) has proven just as inexpedient, since they too must first be installed and read using further devices. It is therefore desirable to be able to provide a visualization system which makes do without the use of additional components (such as separate cameras and a marker system).

The use or application of structured light on surfaces for capturing the three-dimensional form of the surface is known. To this end, a light pattern is projected onto an object, that is to say in this case the patient or a body part thereof, and the pattern deformation is observed using a camera. The geometric (three-dimensional) surface structure of the patient body is, as it were, coded in light and thus becomes capturable.

From the research field of virtual reality, it is also known to use head-mounted visualization devices, what are known as head-mounted displays (HMD for short). These are spectacles, the lenses of which can be switched and used both to see through and as a projection surface for digital images. One example of a HMD device is described in more detail in published patent application US 2013/0021373 A1.

In the medical field, however, it is important that the surgeon or the physician carrying out an intervention need not unnecessarily look away from the relevant body structure to obtain further necessary information relating to the body structure under examination (for example X-ray image). For example, it is highly bothersome that the physician must look away from the operating field in order to analyze an X-ray image displayed on a separate monitor.

Medical technology currently lacks systems which combine in a suitable manner image-type surface information in three-dimensional form and image-type depth information of a body segment and fuse them in a spatially resolved manner.

SUMMARY OF THE INVENTION

It is accordingly an object of the invention to provide a visualization system which overcomes the above-mentioned and other disadvantages of the heretofore-known devices and methods of this general type and which provides for a visualization system and method that is executable without additional outlay on the part of the physician or of the user in the operating room. Furthermore, the time and the quality with which in each case the information provided is available should be improved.

With the foregoing and other objects in view there is provided, in accordance with the invention, an intraoperative, marker-less visualization system for visualizing three-dimensional structures during an intervention on a patient by way of an imaging device that moves during image acquisition. The novel system comprises the following elements:

a C-arm projection module for projecting structured light onto a first selected region of a body surface of the patient, said C-arm projection module being integrated in the imaging device and functional while the imaging device moves for image acquisition;

visualization spectacles having a head-mounted device (HMD) projection module for projecting, upon receiving a start signal, structured light onto a second selected region of the body surface of the patient;

a camera system for capturing the structured light projected by said C-arm projection module and by said HMD projection module so as to compute at least one digital image data set of a 3D surface structure by a processor, said camera system being at least partly integrated in one or both of the imaging device or said visualization spectacles;

a synchronization device configured for outputting a trigger signal upon automatically detecting that the first selected region projected by said C-arm projection module matches the second selected region projected by said HMD projection module; and a fusion unit configured for generating, in response to receiving the trigger signal of said synchronization unit, a combined image data set and to output the combined image data set on said visualization spectacles, the combined image data set correlating the image captured by the imaging device with the digital image data set of said camera system of the body surface.

The objects of the invention are achieved by the visualization system, as summarized here, by a method, and by a related control program.

The way in which the object is achieved will be described below with respect to the claimed apparatus or the system. Features, advantages or alternative embodiments mentioned here can also be transferred to the other claimed subject matters and vice versa. In other words, the object-based claims (which are directed for example to a system) can also be developed with the features which are described or claimed in connection with the method, and vice versa. The corresponding functional features of the method are here formed by corresponding object-based modules, in particular by microprocessor or hardware modules.

According to one aspect, the invention relates to a visualization system for visualizing three-dimensional structures during an intervention on a patient by way of an imaging device, for example with a C-arm, comprising:

a C-arm projection module which is intended for projecting structured light onto a first selected region of a body surface of the patient, wherein the C-arm projection module is integrated in the imaging device and while the imaging device moves for image acquisition visualization spectacles which comprise a HMD projection module that is intended for projecting, upon a start signal, structured light onto a second selected region of a body surface of the patient a camera system which is intended for capturing the structured light projected by the C-arm projection module and by the HMD projection module so as to compute at least one digital image data set of a 3D surface structure using a processor, and wherein the camera system is integrated in the imaging device and/or in the visualization spectacles a synchronization device which is intended for outputting a trigger signal once it automatically detects that the first selected region projected by the C-arm projection module matches the second selected region projected by the HMD projection module, or that the respective digital image data sets captured using the camera system match a fusion unit which is intended for generating, in response to the trigger signal of the synchronization unit, a combined image data set and to output it on the visualization spectacles, wherein the combined image data set correlates the image captured by the imaging device and the digital image data set of the camera system of the body surface.

Terms used within the context of this application will be explained in more detail below.

The visualization system comprises a plurality of physical components and is used preferably intraoperatively, that is to say during a surgical intervention. Alternatively, it may be used while capturing image data without surgical intervention, for example when planning same, or in the case of a purely imaging-type measure for examining a patient. The visualization system is marker-less, that is to say it neither uses nor requires the use of markers for capturing spatial or movement data. This represents an important advantage with respect to known systems, since markers do not need to be positioned and maintained. In particular, it is important to ensure during the intervention that the marker signals can also be received without disturbance and are not interrupted, for example by further medical articles in the room.

"Structures" can be organs or body segments in the patient body or can be artificial medical objects, such as implants or surgical material, such as screws, pins or the like.

The imaging device is typically a movable or mobile C-arm which is intended for capturing X-ray images. The present invention can of course also be used for tomosynthesis devices and other imaging modalities, such as for example MRI systems, PET devices etc. According to one aspect of the invention, the imaging device is intended for image data acquisition of structures which are not located on a body surface of the patient but inside the patient.

The C-arm projection module is a device for projecting structured light, such as for example a light pattern or light at different wavelengths or colors. What is important is that the C-arm projection module is integrated directly in the C-arm or in the imaging device. Here, it is secured to a predetermined and thus known position on the C-arm. This position can then be used for later spatial, movement and/or image computations. The C-arm projection module can preferably be secured releasably but fixedly on the C-arm.

Not only the C-arm, but also the visualization spectacles have such a projection module, that is to say the HMD projection module. It is likewise intended for projecting structured light. In particular, both projection modules can be controlled by the same control unit and apply the same type of structured light. The control unit can be integrated as claimed in one embodiment in a processor. It can furthermore also control the temporal performance of the light projection, in particular also in relation between the two projection modules.

The visualization spectacles function as head-mounted field-of-vision device and can also be referred to as a head-mounted display. Variations are conceivable. For example, the spectacles may also be configured as video spectacles, helmet display or simply as an ocular with one spectacle lens or one lens.

The camera system can comprise one or at least two cameras, preferably CCD cameras. The camera system is intended for capturing the applied structured light. If colored light is intended to be applied, the camera system must accordingly be a color camera, otherwise black and white capturing will suffice. Preferably two cameras are provided: one is integrated in the C-arm (for example also as a detachable but fixedly integrated module), and a second one is integrated in the visualization spectacles. The camera system comprises a processor or exchanges data with a separate processor (preferably via a wireless radio link). The processor is a processing unit for computer-based and automatic processing of digital data sets which were captured by the camera system. In particular, the processor generates a digital image data set. In addition, the processor can also carry out further image processing, for example filtering functions, storing data, comparison with predetermined values etc. According to one aspect of the invention, the camera system is intended for capturing three-dimensional surface structures which are not located inside the patient but on a body surface of the patient.

The synchronization device is an electronic component. It serves as a computer-based module for matching the image data captured by the two cameras. In particular, a comparison is carried out in relation to identity or match in a presettable tolerance range with very high accuracy. This identity comparison serves to synchronize the C-arm and the visualization spectacles. This ensures that the projection module of the C-arm and the HMD projection module of the visualization spectacles apply light onto exactly the same body region of the patient. Only in this case, a trigger signal is output.

Upon the trigger signal, the fusion unit can be activated. The fusion unit is likewise an electronic component and serves for generating a combined image data set. The combined image data set comprises a depth image (captured by the imaging device, for example X-ray) and a surface image (captured by the camera system or a camera of the camera system of the body surface). The depth image and the surface image are here spatially correlated. The depth image concerns the same body structure as the surface image and vice versa. The combined image data set is projected onto the visualization spectacles. The viewer thus obtains three different image data sets of the very same body structure at the same time and in the very same physical viewing axis, namely:

the image data set captured by the imaging device (e.g. X-ray image)

the surface image in three-dimensional form, the content of the surface image matching the content of the first image data set, and the pure image when observing the body structure (through the spectacles without spectacle projection or when viewing the body structure directly).

According to one preferred embodiment, the synchronization device is integrated in the visualization spectacles. The same is true for the fusion unit. Alternatively, the above-mentioned electronic components can also be integrated in the processor or in a further processing module connected via a network connection and can thus be arranged outside the visualization spectacles.

According to a further embodiment, the synchronization device and the fusion unit are integrated in one module.

According to a further embodiment, the processor also computes the digital image data set captured by the camera system during a movement, in particular a rotational and/or translational movement of the imaging device, by applying an automatic, computer-based method for optical triangulation. This method is also used when the physician changes his head position with the visualization spectacles, that is to say during a movement of the HMD projection module of the visualization spectacles. Additionally, the distance from the respective camera to the object (here: surface) is captured automatically via a sensor or is read from a memory location, if this is known. The movement parallax here refers to the apparently relative displacement or movement between objects which are located at different distances from the optical capturing system or the viewer (here: camera), which is caused by a change in the position of the viewer or by the movement of the objects relative to the viewer. Objects located further away in this case move apparently more slowly than objects which are located a shorter distance away from the viewer. The movement parallax thus comprises a depth indication which is taken into account when computing in the processor and/or in the fusion unit.

A further way of achieving the object is a visualization method for visualizing three-dimensional structures during an intervention on a patient by way of an imaging device, comprising the following method steps:

capturing an image data set with the imaging device, in particular with a C-arm;

first projection of structured light onto a first selected region of a body surface of the patient with a C-arm projection module that is integrated in the imaging device while the imaging device moves for the purpose of image acquisition;

second projection of structured light onto a second selected region of the body surface of the patient with a HMD projection module that is integrated in a pair of visualization spectacles;

capturing at least one digital image data set with the projected first and/or second selected region for computing a 3D surface structure in the respectively projected region;

outputting a trigger signal if it is automatically ascertained that the first selected region and the second selected region match;

in response to the trigger signal: generating a combined image data set and outputting same on the visualization spectacles, wherein the combined image data set is computed by correlating the image captured by the imaging device with the at least one digital image data set with the computed 3D surface structure.

Other embodiments of the invention here provide deviating sequences of the above-mentioned processing steps. For example, it is also possible to carry out the first projection in a first step, and to capture the X-ray only subsequently.

According to one aspect, the first projection and the second projection are carried out at the same time or within a matching timeframe (that is to say at least with temporal overlap; but it is also possible to be done with different starting times).

According to one aspect, the capturing of the at least one digital image data set is carried out when (at the same time or after) the second projection is carried out. The term "when" here means a temporal condition or a causal condition. That means that the capturing can be carried out only once the projection is carried out or when it is being carried out. The capturing can likewise be carried out within the timeframe in which the projection is also taking place.

According to one aspect, the capturing of the at least one digital image data set is carried out at the same time or within a matching timeframe as the image acquisition using the imaging device.

The above-described embodiments according to the invention of the method can also be in the form of a computer program product with a computer program, wherein the computer is made to carry out the above-described method according to the invention when the computer program is carried out on the computer or on a processor of the computer.

One alternative way of achieving the object is also by way of a computer program with computer program code for carrying out all method steps of the claimed or above-described method when the computer program is carried out on the computer. The computer program can in this case also be stored on a machine-readable storage medium.

One alternative way of achieving the object is provided by a storage medium which is intended for storing the above-described computer-implemented method and is computer readable.

It is within the framework of the invention that not all steps of the method must necessarily be carried out on the very same computer instance, but they can be carried out on different computer instances (comprising computer, processor and further computer-based automatic processing instances). The sequence of the method steps, as explained above, can likewise optionally be varied.

Moreover, it is possible for individual sections of the above-described method to be carried out in a saleable unit and for the remaining components to be carried out in a different saleable unit—what is known as a distributed system.

Other features which are considered as characteristic for the invention are set forth in the appended claims.

Although the invention is illustrated and described herein as embodied in a triangulation-based depth and surface visualization, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 shows an overview-type illustration of an overall structure of an exemplary embodiment of the visualization system according to the invention;

FIG. 2 shows a schematic overview illustration of a pair of visualization spectacles;

FIG. 3 is a schematic overview diagram of a processor for computing a combined image data set; and FIG. 4 is a flowchart illustrating the dataflow of a method according to an exemplary embodiment of the invention.

DETAILED DESCRIPTION OF THE INVENTION

Referring now to the figures of the drawing in detail and first, particularly, to FIG. 1 thereof, there is shown a schematic view of a visualization system which is used in particular during a medical intervention. This can be a surgical intervention or mere image data capturing for planning further steps or can be further measures. The visualization system serves for visualizing or representing three-dimensional patient structures in space. Here, the intention is both to obtain a three-dimensional image of the body surface in a pre-selectable region (region of interest—ROI), and to represent the image captured with an imaging device 10. The imaging device is in particular a mobile C-arm, which can be mounted in mobile fashion and for example on a roller carriage 18. The C-arm serves for capturing X-ray images and/or tomosynthesis images. The invention can of course also be used for other imaging modalities, such as for example magnetic resonance imaging. The following description of the figures, however, mainly concerns itself with an X-ray C-arm 10, since this is a preferred embodiment of the invention, but without limiting the scope of protection of the invention to this embodiment.

The visualization system thus serves for simultaneous representation of the body surface and of depth images of the patient in a region of interest (ROI). What is important is that the physician obtains for example during an intervention at the same time information relating to the body surface and associated image information relating to the structures located under the body surface ("internal" or "depth" structures), such as for example bones, organs, vessels, implants etc. The latter structures can be captured using the C-arm 10. The visualization system according to the invention thus correlates the body surface structures with the body depth structures and displays them on a pair of visualization spectacles 20.

The visualization system is marker-less and requires no placement of markers, whether active markers or passive markers.

The visualization system is illustrated schematically in FIG. 1 and comprises the C-arm 10 and a pair of visualization spectacles 20, which can be configured in the form of spectacles and can be worn on the head by the physician during the intervention. The visualization spectacles 20 can also be referred to as head-mounted field-of-vision device or is known as a head-mounted display. The visualization spectacles 20 can thus also be configured in the manner of a helmet or as a field-of-vision device which merely has one spectacle lens 21. However, it is with preference a pair of visualization spectacles 20 which have two spectacle lenses 21.

The C-arm 10 comprises, as also known in the prior art, at least one X-ray source 12. The term "X-ray source" in this context is not to be understood to be limiting and is intended to refer to an X-ray system made of X-ray emitters. Typically, an X-ray source can consist of a multiplicity of differently arranged X-ray emitters, which are additionally also movable within the C-arm 10 (for example mounted such that they can pivot). As a counterpiece and for capturing the X-rays passing through the patient or through the relevant region of the patient, an X-ray detector is located in the C-arm 10, which is not illustrated in FIG. 1, because it is irrelevant for the understanding of the invention. The C-arm 10 according to the invention includes, in addition to the known components, further physical components, namely:

a C-arm projection module 16, and
a fixedly positioned camera 14.

The C-arm projection module 16 and the camera 14 are fixedly integrated in the C-arm 10. The term "fixedly" in this context means that both physical components have a fixed position which can be used for later computations. However, the two components or one of the components can be secured releasably on the C-arm 10, for example by snapping or latching it/them on. It is important, however, that both the C-arm projection module 16 and the camera 14 have a respectively assigned defined position, in particular with respect to the X-ray source 12. The C-arm 10 moves during the image acquisition about the patient (pivoting movement) and can also be moved in a translational manner. The captured X-ray images are typically passed on to a computer 19, which is connected via a corresponding network connection, for post-processing or further processing. The computer 19 can also be integrated partially or completely directly in the C-arm, however. Moreover, the computer 19 can also be provided as a separate module. It is also within the framework of the invention to provide here a plurality of processors or computers or computer units, which are referred to as a computer 19 on the whole. The individual components or units can also be arranged in a distributed manner.

FIG. 2 schematically shows, by way of an overview, a pair of visualization spectacles, which are designated in the figures in principle with the reference numeral 20. The visualization spectacles 20 comprise a HMD projection module 22, a camera 24 and a processor 25. These components are preferably worn together with the two spectacle lenses 21 in a frame. The HMD projection module 22 serves for projecting structured light onto a second selected region of a body surface of the patient. According to one preferred embodiment, provision is made for the HMD projection module 22 to be activated only after a start signal s is detected. In other words, the HMD projection module 22 remains inactive and does not send any light radiation if no corresponding start signal s can be received. The light projected by the HMD projection module 22 can be a simple light pattern (for example strip pattern) or a color pattern which is applied onto a three-dimensional surface. Owing to a triangulation calculation, distortion caused by the three-dimensional form of the light pattern can be captured by a camera, for example the camera 24 of the visualization spectacles 20, and a processor 25 can calculate which is the associated image data of the 3D surface structure. The image data of the 3D surface structure can thus be computed and visualized. For capturing the projected light pattern, the camera 24 is provided. Alternative embodiments here make provision for another camera which can be located for example in the C-arm 10, or other cameras can be made available that are already arranged about the OP field during the intraoperative intervention.

The processor 25 of the visualization spectacles 20 serves for generating a digital image data set of the three-dimensional body surface. The computation can be carried out by a computing module which comprises an algorithm based on optical triangulation computation.

The processor 25 comprises interfaces 25i, 25ii. The input variables which are read via the input interfaces 25i, 25ii are, in particular, the digital image data sets which were captured with the camera 14 on the C-arm 10 and with the camera 24 on the visualization spectacles 20.

In FIG. 3, the components of the processor 25 are illustrated schematically in more detail. The respective image data set which was captured with the camera 14 is supplied via the processor input interface 25i to the processor 25. The digital image data set which was captured using the visualization spectacles camera 24 is supplied via the processor input interface 25ii to the processor 25. As already explained above, it is also possible to provide only one camera as the camera system. In this case, the one camera must then capture both the projected first light pattern of the C-arm projection module 16 and the projected second light pattern of the HMD projection module 22. In these cases, the captured image data are supplied via a shared interface or via different interfaces to the processor 25, which then further processes the captured image data. To this end, the processor 25, as illustrated in more detail in FIG. 3, comprises a synchronization device 30 and a fusion unit 32.

The synchronization device 30 is intended for outputting a trigger signal ts if it can be automatically ascertained that the first selected region projected by the C-arm projection module 16 matches the second selected region projected by the HMD projection module 22. In other words, the synchronization device 30 synchronizes the C-arm 10 and the visualization spectacles 20 by way of the applied first and second light patterns. What is crucial is that the first light pattern or the first selected region is emitted by the C-arm projection module 16, and the second light pattern or the second selected region is projected by another projection module, specifically the HMD projection module 22 (of the visualization spectacles 20). The time period in which the C-arm projection module 16 projects a light pattern and the time period in which the HMD projection module 22 applies a light pattern do not necessarily have to coincide. However, the two time periods preferably have an overlap.

The processor 25 comprises the fusion unit 32. The fusion unit 32 is intended for generating a combined image data set kBD if it has received a trigger signal ts from the synchronization unit 30. This is intended to ensure that the fusion unit 32 is activated only if this is necessary, and in particular if the physician views, using his field-of-vision spectacles 20, exactly that region in which the C-arm 10 produces X-ray images or X-ray-based images (for example slice images). As indicated schematically in FIG. 3, the trigger signal ts can also be passed on to further modules which are located externally to and outside the processor 25. Moreover, the trigger signal ts can also be passed on to modules which are located outside the visualization spectacles 20. However, the trigger signal ts is typically passed on at least to the fusion unit 32 so as to inform the latter that the combined image data set kBD is to be generated. The combined image data set kBD is then projected onto the two spectacle lenses 21.

The combined image data set kBD thus comprises both the X-ray image captured by the C-arm 10 in a region of the patient and the three-dimensional surface image on the respective body surface of the patient. Here, the two image data sets are correlated. This means that the body surface image data set and the depth image data set are matched to each other in terms of a spatial relationship. This ensures that the respective depth image and the body surface image come from exactly the same position. This produces the essential, advantageous technical effect that the physician, while examining the patient and/or operating, obtains, at one glance and without having to avert his head (for example in order to look at a separate monitor), information relating both to the body surface and to the situation in the body depth of the body structure to be respectively treated. Moreover, he simultaneously obtains a third item of image information, specifically the observed body region which is currently in his field of vision. He would also see the latter if he were to look at the patient without any further technical additional instruments (in particular without visualization spectacles and without X-ray).

The physician in principle simultaneously obtains three items of image information relating to the same body region, namely:
body depth information, e.g. using the X-ray image,
body surface information relating to the three-dimensional forms of the surface, captured using the camera system 14, 24, and
the native field of vision through the physician's observation.

The physician can thus obtain the maximum amount of image information within a very short time so he is able for example to place a screw for screwing in an implant at the correct location on the body surface such that the screw also strikes the implant internally at the correct location and under the correct angle. The physician obtains the latter information via the X-ray image information. This information is highly important and advantageous especially if the physician undertakes a minimally invasive intervention without opening up a patient. This means an advantage especially in terms of time and quality for surgical procedures, since incorrect positioning of instruments and/or tools can be avoided.

A possible sequence of a visualization method according to the invention will be explained in more detail below with reference to FIG. 4:

After the start of the system, an X-ray image is captured in step A. To this end, it is possible to select a region of interest (ROI) in advance.

In step B, a first projection of structured light using the C-arm projection module 16 takes place.

After a start signal s is captured, a second projection of structured light using the HMD projection module 22, which is located on the visualization spectacles 20, takes place in step C.

In one preferred embodiment, the processor 25 controls the application of the first light pattern in step B and the application of the second light pattern in step C. Typically, the same light pattern is projected. However, alternative embodiments can make provision for deviating control measures here such that the C-arm projection module 16 and the HMD projection module 22 emit different forms of structured light (different patterns, different colors etc.).

In step D, the digital image data set is captured. The digital image data set comprises the image data of the respective body surface captured with the camera system 14, 24. The digital image data set can be computed preferably in the processor 25. The digital image data set preferably relates to a three-dimensional surface structure of the projected region. The digital image data set is characterized by a further aspect in that it contains no depth information. This means that the digital image data set comprises only image data of the body surface and no image data relating to the interior of the body.

In step F, a case discrimination takes place. In this step, a check is carried out as to whether the first projected region matches the second projected region such that they are identical. This serves especially for synchronizing the C-arm 10 with the visualization spectacles 20. If the regions do not match, it can be assumed that the physician is viewing a different region with his visualization spectacles 20 than the region that is targeted by the X-ray device 10 and of which the depth image information is captured. In this case, it is possible to branch back to step B, such that the projection of the two light patterns is activated again.

In the other case, that is to say if the first projected region does match the second projected region, the trigger signal ts is output in step G.

In step H, a combined image data set kBD is generated. The combined image data set comprises the depth image information and the (three-dimensional) body surface information. Both image data sets are matched in a spatially resolved manner and are merged to form a fusion image.

In step I, the computed combined image data set kBD is output on the visualization spectacles 20 and in particular on both spectacle lenses 21 thereof.

As is illustrated in FIG. 4, the method can then be performed iteratively again in that the two projection modules once again project structured light and the method is carried out again. In the other case, and especially if sufficient information has been made available, the method can also end.

What is essential for the visualization system and method according to the invention is that the physician, when activating the visualization function, always obtains an automatically updated computed combined image data set kBD, which automatically matches his field-of-vision device or his field of vision. Without having to avert his head and his gaze, he can access body surface information and body depth information at the same time.

During the pivoting or rotational movement of the C-arm 10, the light pattern projected by the C-arm projection module 16 changes. Furthermore, the form of the projected light changes on account of the differing three-dimensional body surface of the patient located on the operating table. These optical data are transferred, using an optical triangulation method, into a virtual body surface of the patient. Since the three-dimensional X-ray data and the body surface data captured by the camera system 14, 24 are correlated, which is possible on account of the fixed arrangement of the respective projection modules 16, 22 and the cameras 14, 24, the physician can obtain the impression that, upon activating the visualization according to the invention, he obtains in his field of vision a quasi transparent impression of the body area and can thus see through the body surface.

Invariably, only the current image data in the combined image data set kBD are visualized and displayed on the visualization spectacles 20. This ensures that the physician always obtains exactly that additional information (body surface information, body depth information) that matches the region onto which he is currently looking. Furthermore, by using the start signal s and the trigger signal ts, it is made possible that the physician need not bother with unnecessary additional information. If no activation signal s, ts can be captured, no image data set and in particular no combined image data set kBD is displayed on the spectacle lenses 21 of the visualization spectacles 20. In this case, the visualization spectacles 20 do not function as projection means, but the physician obtains the same visual result as if he were to work without visualization spectacles 20.

If the visualization system is activated and the physician wishes to obtain additional image information (depth information, surface information), he will obtain it always in updated form, and in particular even in the case where he moves his head and looks at a different region on the body surface of the patient. This has the effect that the physician using the visualization spectacles 20 can see "through," as it were, exactly that region of the body which he currently observes, in the manner of a magnifying glass.

According to one aspect, the depth information is captured (by means of the imaging device 10) and the body surface information is captured (by means of the camera system 14, 24) by the projection of structured light at the same time. This means that, while the imaging device 10 captures X-ray images, the two projection modules 16, 22 are also activated in order to apply the structured light in the selected first and second regions.

The terms "selected first/second region" were used above since it is possible in one configuration phase to project the structured light onto only one body region of interest. This makes it possible that no unnecessary image surface data need to be collected. Generally, only the region located around the surgical intervention is of interest, such that it suffices to set the projection modules such that they illuminate only one selected region. According to one alternative embodiment, provision is made for the selected first/second region to be formed from the complete first/second region.

In conclusion, mention should be made of the fact that the description of the invention and the exemplary embodiments are in principle not to be understood to be limiting with respect to a specific physical implementation of the invention. In particular, it is obvious to a person skilled in the art that the invention can be implemented in a form in which it is distributed partially or completely in software and/or hardware and/or among a plurality of physical products—in particular including computer program products.

The following is a summary list of reference numerals and the corresponding structure used in the above description of the invention:

- 10 imaging device, in particular C-arm X-ray device
- 12 X-ray source
- 14 camera in the C-arm
- 16 C-arm projection module
- 18 roller carriage for supporting the C-arm
- 19 computing unit or computer
- 20 visualization spectacles
- 22 HMD projection module
- 24 camera in visualization spectacles
- 25 processor
- 21 spectacle lenses
- 25i processor input interface
- 25ii further processor input interface
- 30 synchronization device
- 32 fusion unit
- ts trigger signal
- kBD combined image data set
- s start signal
- A capture X-ray image
- B first projection of first light pattern using C-arm projection module 16
- C second projection of second light pattern using HMD projection module 22
- D capture digital image data set
- F automatic check: does first projected light pattern match second projected light pattern identically?
- G output trigger signal ts
- H generate combined image data set kBD
- I output of combined image data set kBD on visualization spectacles 20

The invention claimed is:

1. An intraoperative, marker-less visualization system for visualizing three-dimensional structures during an intervention on a patient, the system comprising:

an imaging device mounted for moving during image acquisition;

a C-arm structured light projector for projecting structured light onto a first selected region of a body surface of the patient, said C-arm structured light projector being integrated in the imaging device and functional while the imaging device moves for image acquisition;

visualization spectacles having a head-mounted device (HMD) projector for projecting, upon receiving a start signal, structured light onto a second selected region of the body surface of the patient;

a camera system for capturing the structured light projected by said C-arm structured light projector and by said HMD projector, said camera system including at least one camera, said camera being integrated in a device selected from the group consisting of the imaging device and said visualization spectacles;

at least one processor;

said at least one processor programed for computing at least one digital image data set of a 3D surface structure from the structured light captured by said camera system;

said at least one processor programed for generating a trigger signal upon detecting that the first selected region projected by said C-arm structured light projector matches the second selected region projected by said HMD projector; and said at least one processor programed for generating, in response to the trigger signal, a combined image data set and to output the combined image data set on said visualization spectacles, the combined image data set correlating the image captured by the imaging device with the digital image data set of said camera system of the body surface.

2. The intraoperative visualization system according to claim 1, wherein said at least one processor is integrated in said visualization spectacles.

3. The intraoperative visualization system according to claim 1, wherein said at least one processor is programed to also compute the digital image data set captured by said camera system during a movement by applying a computer-based method for optical triangulation.

4. The intraoperative visualization system according to claim 3, wherein said at least one processor is programmed to compute the digital image data set captured by said camera system during a rotational and/or translational movement of the imaging device, and/or during a movement of said HMD projector of said visualization spectacles.

5. The intraoperative visualization system according to claim 1, wherein said imaging device is configured for image data acquisition of structures that are not located on a surface of the patient but inside the patient.

6. The intraoperative visualization system according to claim 1, wherein said camera system is configured for capturing three-dimensional surface structures that are not located inside the patient but on a surface of the patient.

7. An intraoperative marker-less visualization method for visualizing three-dimensional structures during an intervention on a patient, the method comprising the following steps:

providing an imaging device mounted for moving during image acquisition;

capturing an image data set with the imaging device;

projecting a first projection of structured light onto a first selected region of a body surface of the patient with a C-arm structured light projector that is integrated in the imaging device while the imaging device moves during image acquisition;

projecting a second projection of structured light onto a second selected region of the body surface of the patient with a head-mounted device (HMD) projector that is integrated in visualization spectacles;

capturing at least one digital image data set, including the projected first and/or second selected region;

computing a 3D surface structure in the respectively projected region;

upon ascertaining that the first selected region and the second selected region match one another, outputting a trigger signal;

in response to receiving the trigger signal, generating a combined image data set by correlating the image captured by the imaging device with the at least one digital image data set with the computed 3D surface structure, and outputting the combined image data set on the visualization spectacles.

8. The intraoperative marker-less visualization method according to claim 7, which comprises projecting the first projection and the second projection simultaneously.

9. The intraoperative marker-less visualization method according to claim 7, which comprises projecting the first projection and projecting the second projection at times that at least partially overlap each other.

10. The intraoperative marker-less visualization method according to claim 7, which comprises capturing the at least one digital image data set when the second projection is carried out.

11. The intraoperative marker-less visualization method according to claim 7, which comprises carrying out the capturing of the at least one digital image data set simultaneously with the image acquisition using the imaging device or carrying out the capturing of the at least one digital image data set and performing the image acquisition using the image device at times that at least partially overlap each other.

12. An intraoperative marker-less visualization method for visualizing three-dimensional structures during an intervention on a patient, the method comprising the following steps:

providing an imaging device mounted for moving during image acquisition;

capturing an image data set with the imaging device;

projecting a first projection of structured light onto a first selected region of a body surface of the patient while the imaging device moves during image acquisition;

projecting a second projection of structured light onto a second selected region of the body surface;

capturing at least one digital image data set, including the projected first and/or second selected region;

computing a 3D surface structure in the respectively projected region;

upon ascertaining that the first selected region and the second selected region match one another, outputting a trigger signal;

in response to receiving the trigger signal, generating a combined image data set by correlating the image captured by the imaging device with the at least one digital image data set with the computed 3D surface structure, and outputting the combined image data set on visualization spectacles.

* * * * *